United States Patent [19]
Isobe et al.

[11] Patent Number: 5,272,746
[45] Date of Patent: Dec. 21, 1993

[54] METHOD OF EVALUATING A DEGREE OF FATIGUE IN A STRUCTURAL MATERIAL

[75] Inventors: Yoshihiro Isobe; Atsushi Kamimura; Kazuhiko Aoki, all of Ohsaka, Japan

[73] Assignee: Genshi Nenryo Kogyo Kabushiki Kaisha, Tokyo, Japan

[21] Appl. No.: 11,337

[22] Filed: Jan. 29, 1993

[30] Foreign Application Priority Data

Feb. 5, 1992 [JP] Japan .................................. 4-047710

[51] Int. Cl.$^5$ .............................................. G01N 23/20
[52] U.S. Cl. .......................................... 378/72; 378/71
[58] Field of Search ............... 378/72, 71, 70, 86, 378/89, 207

[56] References Cited

U.S. PATENT DOCUMENTS 4,404,682  9/1983  Hayashi et al. ........................ 378/72
4,709,383  11/1987  Goto et al. ............................ 378/72

FOREIGN PATENT DOCUMENTS 0084131  5/1984  Japan ..................................... 378/72

*Primary Examiner*—David P. Porta
*Attorney, Agent, or Firm*—Frishauf, Holtz, Goodman & Woodward

[57] ABSTRACT

A method of evaluating the degree of fatigue in a material to be inspected before the occurrence of a microcrack from data measured nondestructively through the measurement of diffracted beams of X-rays. A fatigue test is performed by applying a predetermined class of repeating stress predicted in a service environment of the material to be inspected to a reference piece of a quality corresponding to the material. A diffracted X-ray measurement is performed on the reference piece at a plurality of points of time during the fatigue test so that in accordance with the measurement results a fatigue characteristic curve is obtained which corresponds to the relation between the integrated amounts of the repeating stress and the intensities of the diffracted beams of X-rays. The diffracted X-ray measurement on a measuring portion of the material to be inspected is effected at each of at least two points of time in a service environment and the rate of change between the measured diffracted X-ray beam intensities is compared with the fatigue characteristic curve. In this way, the degree of fatigue in the material to be inspected as well as its remaining life up to the point of fatigue failure are obtained.

6 Claims, 3 Drawing Sheets

METHOD OF EVALUATING A DEGREE OF FATIGUE IN A STRUCTURAL MATERIAL

BACKGROUND OF THE INVENTION

1. Field of the Invention

The present invention relates to a method of inspecting and evaluating the degree of failure in a structural material, e.g., metal due to fatigue by a nondestructive inspection technique.

2. Description of the Prior Art

A variety of nondestructive inspection methods have heretofore been utilized for the purpose of evaluating the soundness of materials to be inspected, e.g., various materials and structures with respect to their structural construction, quality, strength as well as their shape, etc., by utilizing the detected results of their physical properties without destroying the materials or structures being inspected. The principal nondestructive inspection methods heretofore used for material inspection purposes may for example by classified as follows.

1. Radiographic examination

If any defect such as a microcrack exists in an object, the intensity of a radiation (e.g., X-rays or γ-rays) transmitted through the defective portion is increased as compared with the radiation transmitted through the sound portion. Thus, a film sensitive to the radiation is arranged at the back of the object to be examined so that the shape of the defect is photographed on the photographic film and the soundness of the object under examination is checked from the photographic image produced.

2. Ultrasonic examination (a) Pulse-echo method; A very short ultrasonic pulse in propagated into an object to be examined and an echo reflected from a defect, e.g., a microcrack inside the object is received thereby detecting the position, size, etc., of the defect.

(b) Transmission method; A transmission probe sends an ultrasonic wave in the form of a continuous wave or pulse wave and the ultrasonic wave transmitted through a material to be examined is received by a receiving probe thereby observing the position, size, etc., of a defect from the intensity of the received wave.

(c) Resonance method; A high-frequency voltage of a continuously varying frequency is applied to a probe so that the resulting resonant stationary wave due to the thickness of a material to be examined is measured to detect the thickness of the material under examination.

3. Eddy-current examination

A defect such as a crack in a piece to be examined is detected on the basis of the relation between the intensity of an alternating magnetic field generated from a coil and the generation distribution condition of a magnetic field due to eddy currents caused in the piece by the alternating magnetic field. While the detection sensitivity is generally low as compared with the ultrasonic method, its sensitivity is good for particular types of cracks and therefore it is frequently used as auxiliary means for the ultrasonic inspection.

Generally, when a metallic material is subjected to the action of a repeating stress or the like, the sliping of the crystal grains within the material is caused and it is followed by the occurrence of a microcrack. If the crack grows further, it eventually leads to a fatique failure. Then, in this case, a large part of the time period up to the point of the fatique failure in the material accounts for a microscopic change at the crystal lattice level before the occurrence of the microcrack.

The nondestructive inspection techniques heretofore used for the purpose of evaluating the degree of fatique have been mainly intended for the detection of the size, shape and position of such microcrack which has already been caused and therefore these techniques have been capable of evaluating the degree of fatique in a material only at the last stage leading to the fatique failure of the material.

SUMMARY OF THE INVENTION

It is the primary object of the present invention to provide a method of measuring and evaluating the degree of fatique in a material to be inspected, e.g., metal by a nondestructive inspection technique before reaching a point where the material fails, that is, before the occurrence of a microcrack.

The basic concept of the present invention is based on the fact that when a material having a crystal structure, e.g., metallic material is subjected to the irradiation of X-rays, the resulting X-ray diffraction peak (amplitude level or energy) data show characteristic variations due to the progress of fatigue in the material, paticularly a sign of reaching the point of occurrence of fatique failure.

In accordance with a characteristic aspect of the present invention, there is thus provided a method of evaluating the degree of fatigue in a structural material and the method includes the steps of performing a fatique test by applying at least one of predetermined kinds of repeating stresses such as bend, tension and compression, torsion and impact which are predicable in the service environment of the material to be inspected to a reference piece of a quality corresponding to the material, measuring the intensity of the diffracted X-rays of a predetermined diffraction angle generated from the irradiated portion of the reference piece by X-ray radiation at a plurality of points of time during the interval between the time that the application of the repeating stress to the reference piece is started and the time that failure of the reference piece is caused, obtaining from the measurement results a fatique characteristic curve corresponding to the relation between the integrated amounts of the repeating stress (as represented by the numbers of times of application or the time period of application) and the diffracted X-ray intensities, irradiating the X-rays on a measuring portion of the material to be inspected and measuring the intensity of diffracted X-rays of the predetermined diffraction angle produced from the measuring portion, and comparing the rate of change between the diffracted X-ray intensities measured with respect to the material at least at two points of time in the service environment with the fatique characteristic curve to determine the degree of fatique in the material and, if neccessary, the remaining life until the occurrence of a fatique failure.

In accordance with the present invention, the diffracted X-ray intensity to be measured may be either the peak level (amplitude) or the peak area (energy) of the diffracted X-rays. This measurement is effected during the measuring step with respect to the reference piece and during the measuring step with respect to the material to be inspected, respectively. During the measuring step for the reference piece, a given repeating stress is applied to the reference piece by the technique of a fatique test and also the stress application operation is interupted each time a predetermined integrated stress amount is reached, thereby performing the diffracted X-ray measurement on the reference piece during this interruption period. On the other hand, during the measuring step for the material to be inspected, if the material to be inspected is a structural material, for example, as in the case of a plurality of periodic inspections, a plurality of diffracted X-ray measurements are performed on the material to be inspected in its service conditions at different points of time in the service conditions. These diffracted X-ray measurements for the material in the service conditions may be performed with respect to the material removed temporarily from its place of use or alternatively the measurements may be effected with respect to the material in its place of use as such if a probe for diffracted X-ray measuring purposes is prepared.

Thus, in accordance with the present invention, it is only neccessary to irradiate X-rays on a part of a material to be inspected and measure the diffracted X-ray intensity of a given diffraction angle by a diffracted X-ray probe or the like and therefore not only there is no need to subject the material to sampling but also the material is not destoyed by the measurement. The diffracted X-ray measurement for the material to be inspected is effected for example at the initial time instant as the structural material and at the later time instant when the application of a certain integrated amount of repeating stress is attained by the subsequent use of the material or alternatively the measurement is effected at two different points of time during the service. In either case, the rate of change of the diffracted X-ray intensities of the given diffraction angle measured on the material to be inspected at the two points of time involves information corresponding to the change of the crystal structure in the material before the occurrence of a crack and thus this rate of change serves as an indication of the evaluation of the fatique due to the action of the repeating stress applied to the material during the time interval between the two points of time. On the other hand, at least one of many kinds of repeating stresses predicted in the service emvironment of the material such as bending, tension and compression, torsion and impact is applied to a reference piece of the same quality as the material to be inspected and the relation between the integrated amounts of the applied stress and the diffracted X-ray intensities of the given diffraction angle is obtained as a fatigue characteristic curve.

In accordance with the present invention, this fatigue characteristic curve obtained for the reference piece is utilized as indices to evaluate the degree of fatigue in the material under examination. More specifically, a fatigue characteristic curve showing the variations of a specified diffracted X-ray intensity relative to integrated amounts of a certain kind of repeating stress is preliminarily obtained for a reference piece of a quality corresponding to a material to be inspected and the rate of change due to the integrated applied stress amounts of the corresponding diffracted X-ray intensities measured with respect to the material under examination is compared with the fatigue characteristic curve whereby depending for example on the determination of the sign of the rate of change, the degree of fatigue in the material under examination at the time of the measurement is evaluated and the remaining life of the material with respect to the fatigue is obtained without destroying the material.

The above-mentioned fatigue characteristic curve can be obtained as a curve on a rectangular coordinate system in which the abscissa represents the integrated stress amount, e.g., the number of times of application of a repeating stress and the ordinate represents the diffracted X-ray intensity. In this case, while the curve varies depending on various factors such as the quality, degree of processing and fatigue condition of the material, there are instances where by preliminarily obtaining a fatigue characteristic curve according to the coordinate axes scales normarized by the required fatigue conditions, etc., it is possible to represents the necessary fatigue characteristic curves by a single curve even in the case of materials to be inspected which are different in quality, degree of processing, fatigue condition, etc. Thus, as for example, in the rectangular coordinate system for the fatigue characteristic curve the integrated stress amounts on the obscissa can be represented in terms of ratios to the integrated stress amount attained at the point of fatigue failure of a reference piece and also the diffracted X-ray intensities on the ordinate can be represented in terms of ratios to the intial X-ray intensity measured with respect to the reference piece to which the repeating stress is not applied as yet. By virtue of such normalization, even in the case of materials to be inspected which are different in quality, degree of processing fatigue condition, etc., the evaluation of the degree of fatigue and the estimation of the remaining life of materials to be inspected can be effected from a single common fatigue characteristic curve.

From the foregoing it will be seen that since the measurement results of the diffracted X-ray intensities involve various internal information such as the crystal structure of a material to be inspected, by measuring variations in the diffracted X-ray intensity due to fatigue, it is possible to evaluate the degree of fatigue. Thus, in accordance with the present invention the degree of fatigue damage of a material to be inspected, e.g., metal prior to the occurrence of a microcrack can be evaluated from the measurement results by a nondestructive measurement technique.

The present invention is well suited for evaluation of the degree of fatigue in ordinary machine parts as well as various structural materials such as construction, building, aircraft, shipping, automotive vehicle, nuclear reactor and their incidental ewquipment and the invention is applicable to any materials to be inspected including not only such metals as stainless steels and stainless steel alloys but also those materials having the ordinary crystal structure.

The above and other objects, features and advantages of the present invention will become more apparent from the following detailed description of preferred embodiments of nonlimiting nature when taken in conjunction with the accompanying drawings.

DESCRIPTION OF THE PREFERRED EMBODIMENTS

Figure 1:
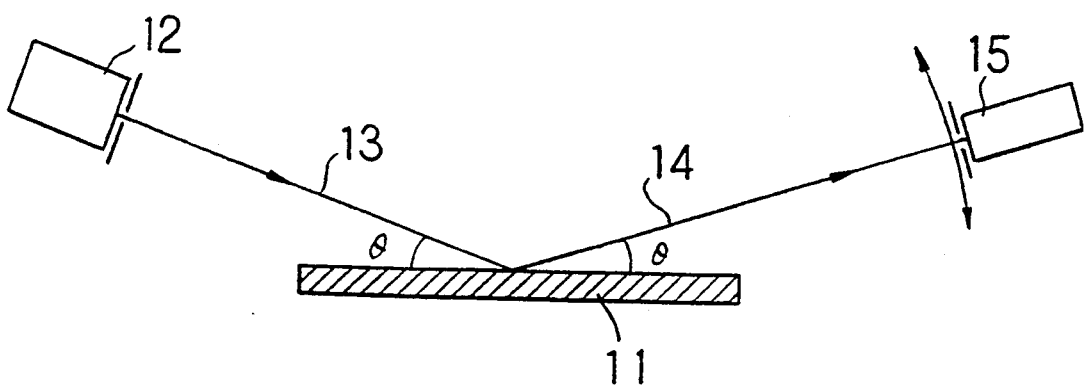
FIG. 1 is a diagram schematically showing the manner in which the measurement of diffracted X-ray intensity is effected on a material to be inspected and a reference piece in accordance with a preferred embodiment of the present invention.

Referring to FIG. 1, an object 11 to be measured is a material to be inspected or a reference piece and an incident X-ray beam 13 from an X-ray source 12 is irradiated with an incidence angle $\theta$ on a measuring portion on the surface of the object 11. A diffracted X-ray beam 14 of a diffraction angle $\theta$ is emitted from the irradiated portion and it is directed to an X-ray detector 15. The detector 15 applies a detection signal to a measured signal processing unit which is not shown, thereby obtaining a peak value of the diffracted X-ray beam of the diffraction angle $\theta$ from the irradiated portion and measuring position data as well.

The specific operations which will be performed for the principal measurements in accordance with the present embodiment include the following processes.

Figure 2:
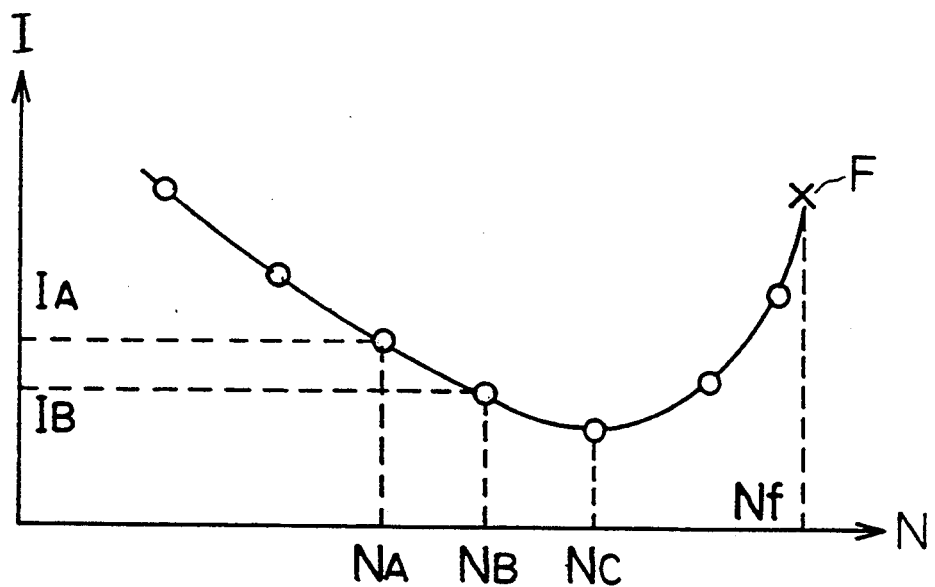
FIG. 2 illustrates an examplary fatigue characteristic curve obtained for the reference piece.
Figure 3:
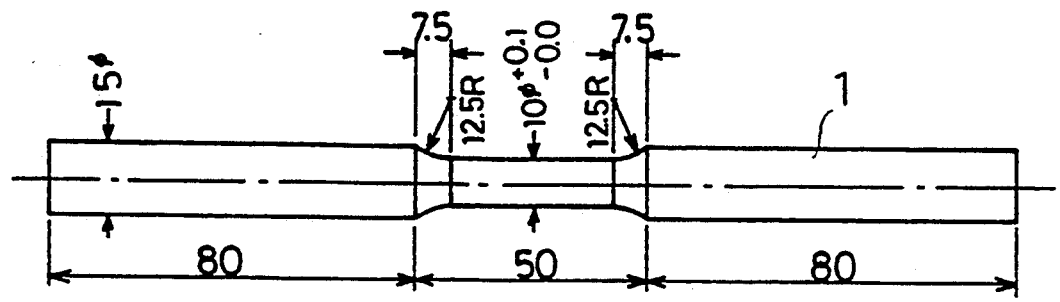
FIG. 3 shows an example of the external shape and size (in unit of mm) of the reference piece.

| | |
|---|---|
| Process 1: | After preparing a reference piece of a quality corresponding to an object subject to degree of fatigue evaluation or a material to be inspected, at least one of different kinds of repeating stresses predicted in the service environment of the material to be inspected, e.g., bend, tension and compression, torsion and impact is applied to the reference piece and a peak value of the diffracted X-ray intensity is measured by a diffracted X-ray measurement of a specific diffraction angle when a certain integrated amount of the applied repeating stress is attained. This integrated amount is reprented by a number of applications of a stress, e.g., a number of times of bending. |
| Process 2: | The resulting peak intensity of the diffracted X-ray beam (peak level or peak area) and the then current number of stress applications are plotted on a rectangular coordinate system. It is to be noted that this operation may for example be performed by a data processing within the computer added to the measuring apparatus. |
| Process 3: | By repeating the processes 1 and 2 respectively at intervals of different numbers of stress applications, a characteristic (fatique characteristic curve) showing the relation between the numbers of stress applications and the diffracted X-ray intensities is obtained. FIG. 2 shows an example of the resulting fatigue characteristic curve and FIG. 3 shows by way of example the shape and size of the reference piece. |
| Process 4: | The same diffracted X-ray measurement as the process 1 is performed with respect to the material to be inspected to obtain a value of the first diffracted X-ray intensity. |
| Process 5: | With respect to the material to be inspected, the same diffracted X-ray measurement is effected in the like manner as the Process 4 after the repeating stress has been applied in the service environment over a certain period of time to obtain the second diffracted X-ray intensity value. |
| Process 6: | In accordance with the ratio of the first value obtained by the process 4 to the second value obtained by the process 5, the rate of change of the diffracted X-ray intensity is obtained with respect to the material under examination. |

In accordance with the rate of change obtained by the process 6 and the fatigue characteristic curve obtained by the process 3, it is now possible to grasp the degree of fatigue in the material to be inspected.

The degree of fatigue can for example be obtained in the following manner.

Referring now to FIG. 2, the abscissa N represents the number of applications of stress to the reference piece and the ordinate I represents the diffracted X-ray intensity. Assuming that $I_A$ and $I_B$ respectively represent the diffracted X-ray intensities measured when the number of stress applications are $N_A$ and $N_B$, respectively, the rate of change ($\Delta I/\Delta N$) of the diffracted X-ray intensity relative to the numbers of stress applications during the interval is given by the following equation $$\Delta I/\Delta N = (I_B - I_A)/(N_B - N_A)$$

In the case of FIG. 2, for example, the rate of change becomes nagative before the number of applications $N_C$ indicative of the minimum diffracted X-ray intensity and it becomes 0 at the number of applications $N_C$. The rate of change becomes positive after the number of applications $N_C$.

Therefore, by determining at least the sign of the rate of change ($\Delta I/\Delta N$) obtained by the process 6, it is possible to know whether the degree of fatigue in the material is in the region before or after the number of applications $N_C$ indicating the minimum diffracted X-ray intensity on the fatigue characteric curve obtained with respect to the reference piece and the remaining life (degree of fatigue) up to a stress application time $N_f$ or the point of fatigue failure can be predicted from the fatigue characteristic curve with a considerably high degree of accuracy. Of course, depending on the quality or the like of the indivisual structural materials as materials to be inspected, a sign leading to the fatigue failure point on the fatigue characteristic curve shows itself in the magnitude of the rate of change or the like and thus it is also possible to evaluate the remaining life of the material according to the magnitude of the rate of change.

It is to be noted that as regards the interval ($\Delta N$) at which the evaluation of the degree of fatigue is actually effected on a material to be inspected, it is preferable to determine the required interval from the fatigue characteristic curve preliminarily obtained for the corresponding reference piece.

While, this fatigue characteristic curve varies depending on the quality, degree of processing, fatigue condition, etc., if the fatigue characteristic curve is preliminarily normalized by the necessary fatigue conditions, it is possible to determine the degree of fatigue and the remaining life in accordance with the normalized fatigue characteristic curve with repsect to materials to be inspected which are different in quality, degree of processing, fatigue conditions, etc. In other words, by using for example the ratios obtained by dividing the numbers of stress applications on the abscissa of FIG. 2 by the number of stress applications at the fatigue failure point and the ratios obtained by dividing the diffracted X-ray intensities on the ordinate by the diffracted X-ray intensity (initial value) attained when the stress is not applied as yet, the required fatigue characteristic curves for materials of different load stresses can be replaced by the single normalized fatigue characteristic curve. Examples:

The evaluation of the degree of fatigue by the diffracted X-ray measurement was effected with respect to a nuclear reactor structural member made of a high-nickel heat-resisting alloy material (tradename: Inconel 718, FCC crystal).

Figure 4:
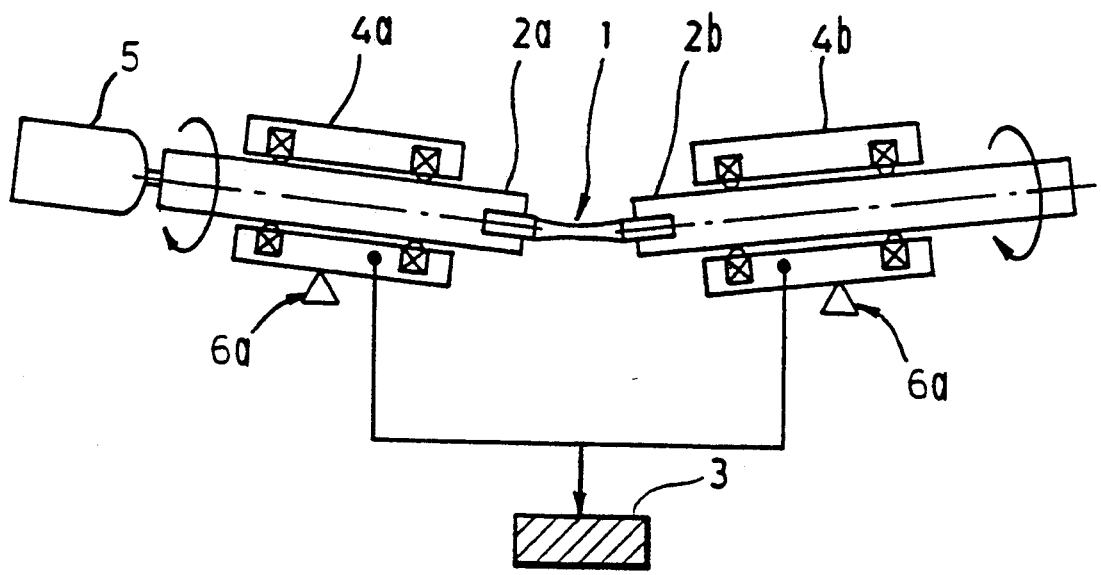
FIG. 4 is a schematic diagram showing the principal parts of an apparatus for repeatedly applying a rotation bend stress as a repeating stress to the reference piece.

Two reference pieces 1 of the same shape and size as shown in FIG. 3 and made of the same alloy material were prepared. A repeating rotation bend stress was applied to these reference pieces 1 by the fatigue testing machine shown in FIG. 4. More specifically, as shown in FIG. 4, this fatigue testing machine comprised bearings 4a and 4b which were respectively tiltably supported by supporting points 6a and 6b and arranged in opposition to each other, rotary chucks 2a and 2b respectively rotatably supported by these bearings, a motor 5 for driving the rotary chuch 2a into rotation, and a weight 3 for applying a load to cause a bending stress to act on the reference piece 1 held between the bearings.

With the ends of the reference piece 1 being gripped by the chucks 2a and 2b, a load was applied to the reference peice 1 while rotating it by the motor 5 and a rotation bend stress repeated every rotation was applied to the reference peice 1, thereby performing a fatigue test by the so-called rotation bend. The load applied to one of the reference pieces by the weight was 75 kg/mm$^2$ and the load applied to the other reference piece was 80 kg/mm$^2$ (the two were maximum evaluated stress values). The frequency of the rotation was 30 Hz in the two cases.

The diffracted X-ray measurement was effected in the following manner. In other words, an X-ray tube lamp used as an X-ray source of an X-ray diffractometer was a Cu tube lamp (with a monochrometer) and the wavelengths of the X-rays produced by impinging the exciting electron beam on the Cu (copper) target were made uniform through the screening by the monochrometer comprised of the graphaite monocrystals. More specifically, the tube voltage and the tube current were respectively 40 kV and 40 mA and the X-rays were irradiated on the test peice by the concentrated beam method using a slit. On the detection side of the X-ray diffractometer, the diffracted X-rays were counted by performing the scanning by an X-ray counter over a range of several degrees centering the peak of the diffracted X-rays produced from the irradiated portion. At this time, the scanning rate was 1.0 deg/min and the sampling step was 0.002 degrees. It is to be noted that the diffracted X-ray measurement was effected by removing the test piece from the fatigue testing machine during the fatigue test as occasion demands.

Figure 5:
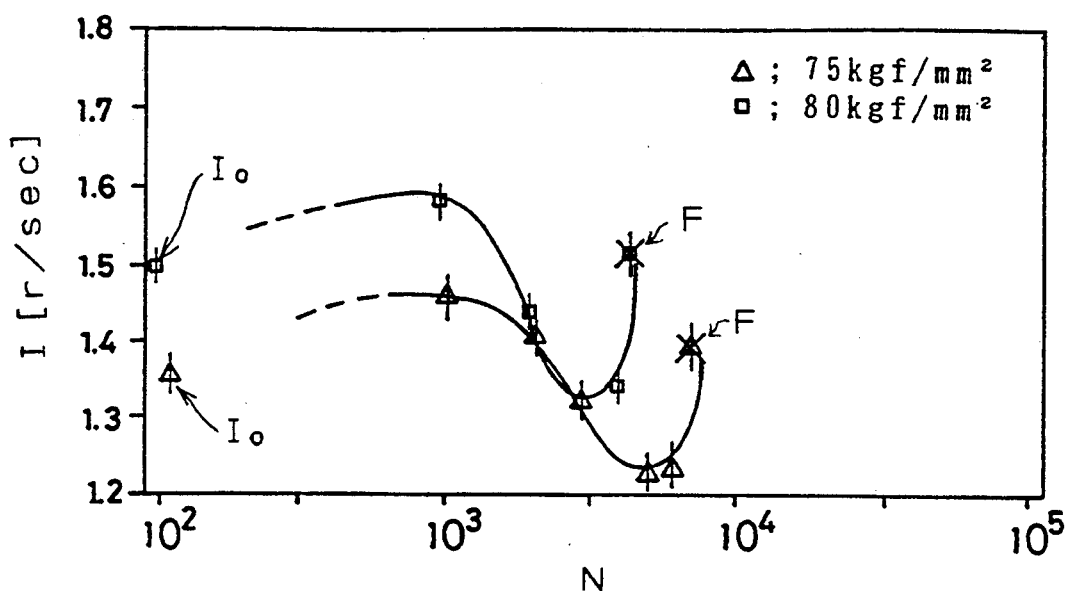
FIG. 5 is a graph in which the diffracted X-ray peak levels at the plane (110) of the reference piece are plotted against the numbers of times of application of the rotation bend stress.

FIG. 5 is a fatigue characteristic diagram in which the peak levels of the diffracted X-rays from the FCC crystal plane (111) of the reference pieces are plotted against the numbers of applications of rotation bend. In the Figure, marks Δ show the measurement results at an applied load of 75 kg/mm$^2$ and marks □ show the measurement results at an applied load of 80 kg/mm$^2$. Also, symbol $I_o$ designates the initial values, and F the fatigue failure points. In either case of the applied loads, the peak level shows characteristic variations of rapidly decreasing and increasing before the point of fatigue failure.

Figure 6:
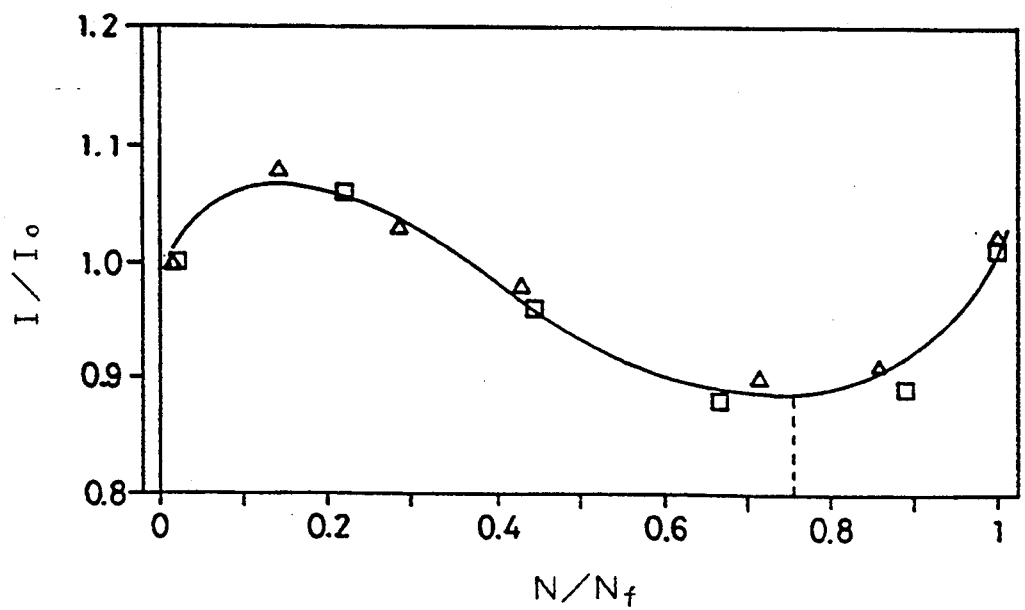
FIG. 6 is a graph corresponding to the graph of FIG. 5 in which the scale of the abscissa is normalized by the numbers of times of stress application leading to a failure and similarly the scale of the ordinate is normalized by the initial values of the diffracted X-ray peak levels.

FIG. 6 is a graph corresponding to the graph of FIG. 5 in which the ordinate and the abscissa are calibrated by representing them by the normalized scales (i.e., the abscissa scale is divided by the numbers of rotation bend applications $N_F$ for failure point and the ordinate scale is divided by the initial value peak levels $I_0$).

While, in FIG. 5, the initial peak levels and the numbers of bends for failure points are separately indicated for the respective applied loads, it is possible to normalize them as mentioned previously and thereby to represent them by a single fatigue characteristic curve as shown in FIG. 6. In other words, it will be seen from FIG. 6 that as for example, when the rate of change of the peak level ratio ($I/I_0$) with respect to the number of bend ratio (N/Nf) is 0, the fatigue life ratio is 0.75, that is, 75% of the life leading to the fatigue failure has been reached. It is to be noted that while, in this embodiment, the peak levels of the diffracted X-rays are measured, curves of the similar tendency can be obtained by measuring the peak areas.

Actually, employing the diffracted X-ray probe, the measurement of diffracted X-rays was effected twice at an interval of given time on the structural component of the previously mentioned alloy used in the nuclear reactor plant under the equivalent measuring conditions and the determination of the rate of change of the diffracted X-ray peak level during the interval resulted in a negative value. From this fact it was found that the fatigue life of this structural component was less than 75% as yet.

The present invention is mainly useful for evaluating the fatigue in structural materials due to the application of a repeating stress. However, if it is possible to obtain any reference hysteresis characteristics by the diffracted X-ray measurement with respect for example to the creep, hot shortness, radioactive radiation brittleness, etc., of structural materials, it is conceivable that methods of evaluating their life can be developed by the similar procedures.

What is claimed is:

1. A method of evaluating a degree of fatigue in a structural material comprising the steps of:

performing a fatigue test on a reference piece of a quality corresponding to a material to be inspected;

irradiating a beam of X-rays on said reference piece at a plurality of points of time during said fatigue test to measure an intensity of a diffracted X-ray beam of a predetermined diffraction angle produced from an irradiated portion;

obtaining a fatigue characteristic curve corresponding to a relation between integrated amounts of repeating stress and said diffracted X-ray intensities by said fatigue test from said measurement results;

irradiating said beam of X-rays on a measuring portion of said material to be inspected to measure an intensity of a diffracted beam of X-rays of said diffraction angle produced from said measuring portion; and determining a degree of fatigue in said material to be inspected by comparing a rate of change between said diffracted X-ray beams measured on said material at least at two points of time interposing therebetween the application of a predetermined kind of repeating stress in a service environment of said material with said fatigue characteristic curve.

2. A method according to claim 1, wherein at least one of a plurality of predetermined kinds of repeating stresses predicted in the service environment of said material to be inspected such as bend, tension and compression, torsion and impact is applied to said reference piece of a quality corresponding to said material during said fatigue test.

3. A method according to claim 2, wherein a number of stress applications is employed as said integrated amount of repeating stress.

4. A method according to claim 1, wherein said step of measuring an intensity of a diffracted beam of X-rays comprises irradiating a beam of X-rays on said reference piece at a plurality of points of time during an interval between a time when the application of said repeating stress to said reference piece is started and a time when failure of said reference piece occurs, and measuring intensities of diffracted beams of X-rays of a predetermined diffraction angle produced from said irradiated portion.

5. A method according to claim 1, wherein said diffracted X-ray measurement on one or another of said reference piece and said material to be inspected is effected by the measurement of diffracted X-ray peak levels or amplitudes.

6. A method according to claim 1, wherein said diffracted X-ray measurement on one or another of said reference piece and said material to be inspected is effected by the measurement of diffracted X-ray peak areas or energies.

* * * * *